(12) United States Patent
Hashimshony et al.

(10) Patent No.: US 9,217,739 B2
(45) Date of Patent: Dec. 22, 2015

(54) TISSUE SAMPLING FOR PATHOLOGICAL STUDY

(75) Inventors: Dan Hashimshony, Givat Ada (IL); Gil Cohen, Jerusalem (IL)

(73) Assignee: DUNE MEDICAL DEVICES LTD., Caesarea (IL)

( * ) Notice: Subject to any disclaimer, the term of this patent is extended or adjusted under 35 U.S.C. 154(b) by 0 days.

(21) Appl. No.: 14/123,249

(22) PCT Filed: Jun. 3, 2012

(86) PCT No.: PCT/IL2012/050196
§ 371 (c)(1),
(2), (4) Date: Dec. 2, 2013

(87) PCT Pub. No.: WO2012/164567
PCT Pub. Date: Dec. 6, 2012

(65) Prior Publication Data
US 2014/0098376 A1    Apr. 10, 2014

Related U.S. Application Data

(60) Provisional application No. 61/492,413, filed on Jun. 2, 2011.

(51) Int. Cl.
*G01N 21/00* (2006.01)
*G01N 33/483* (2006.01)
(Continued)

(52) U.S. Cl.
CPC .............. *G01N 33/4833* (2013.01); *G01N 1/06* (2013.01); *G01N 1/286* (2013.01); *A61B 10/00* (2013.01); *A61B 10/02* (2013.01); *A61B 2019/507* (2013.01); *G06F 19/3406* (2013.01)

(58) Field of Classification Search
CPC ... H01J 37/32935; G01N 21/64; G01N 21/68; G01N 2015/1037; G01J 3/02
USPC ......................................... 356/72–73
See application file for complete search history.

(56) References Cited

U.S. PATENT DOCUMENTS 6,962,587 B2 * 11/2005 Johnson et al. ................. 606/41
2002/0056345 A1   5/2002 Ganser et al.
2004/0085443 A1   5/2004 Kallioniemi et al.
(Continued)

FOREIGN PATENT DOCUMENTS

WO    2008072238 A2    6/2008

OTHER PUBLICATIONS

PCT/ IL2012/ 050196 "International Search Report" (Oct. 5, 2012).

*Primary Examiner* — Abdullahi Nur
(74) *Attorney, Agent, or Firm* — Browdy and Neimark, P.L.L.C.

(57) ABSTRACT

A probe device for use in a tissue inspection system is presented. The probe device comprises a probe body and a control unit at least partially incorporated in the probe body. The probe body carries at least a tissue characterization unit operable for providing sensing data indicative of at least one tissue property at measurement locations in the tissue portion being held by the probe. The control unit comprises: a processor utility for receiving and processing the sensing data and generating measured data indicative of a spatial profile of said at least one tissue property distribution within the tissue portion, and comprises at least one of the following: an imaging utility for receiving said measured data and generating and displaying an image indicative thereof thereby enabling a user to select a region of said tissue portion for further analysis; and a pattern generator module configured for receiving and analyzing said measured data and determining a pattern indicative of an arrangement of regions in said tissue portion, thereby enabling selection of at least one of the regions for further analysis.

20 Claims, 6 Drawing Sheets

| (51) | Int. Cl. | |
|---|---|---|
| | *G01N 1/06* | (2006.01) |
| | *G01N 1/28* | (2006.01) |
| | *A61B 10/00* | (2006.01) |
| | *A61B 19/00* | (2006.01) |
| | *A61B 10/02* | (2006.01) |
| | *G06F 19/00* | (2011.01) |

(56) References Cited

U.S. PATENT DOCUMENTS

2006/0179992 A1   8/2006  Kermani et al.
2006/0253107 A1  11/2006  Hashimshony et al.
2010/0222647 A1   9/2010  Hashimshony et al.

\* cited by examiner

TISSUE SAMPLING FOR PATHOLOGICAL STUDY

FIELD AND BACKGROUND

This invention is generally in the field of tissue characterization and sampling, and relates to a device and method for tissue sampling for pathological analysis.

Surgical pathology is a very important field directed at definitive diagnosis and confirmation of existence or lack of disease types. Performed by skilled pathologists, surgical pathology involves two main stages of examination: (1) macroscopic gross examination and processing, and (2) histopathology, which generally consist of the following. Macroscopic gross examination and processing of surgical specimens (e.g. biopsies) is typically carried out by the bare eye, in order to assess the general macroscopic characteristics of the specimen, and to prepare and process the specimen for histopathology analysis. A set of tissue blocks, typically postage stamp-sized portions of tissue, are gathered to be processed and tissue from these blocks is transferred to slides for the second examination stage (microscopy). Histopathology is the microscopic examination (under a microscope) of histological sections of tissue specimen acquired in the gross examination stage and placed onto glass slides. As only a minority of the tissue from a large specimen can reasonably be subject to microscopic examination, the success of the final histological diagnosis is highly dependent on the skill of the professional performing the gross examination and processing.

The outcome of the above described medical diagnosis procedure is formulated as a pathology report describing the histological findings and the opinion of the pathologist. For instance, in the case of cancer, this represents the tissue diagnosis required for most treatment protocols. Regarding removal of cancer, the pathologist indicates whether the surgical margin is cleared, or not cleared (residual cancer is left behind). The whole examination is significantly time-consuming, and as indicated above, is occasionally subjective and depends heavily on the level of skill the involved professional possesses.

GENERAL DESCRIPTION

There is a need in the art for improving the tissue inspection procedure at the pathology examination stage. The conventional techniques are typically based on an initial visual inspection of a tissue portion by a professional (a so-called bare eye inspection), and as a result the samples/slices removed from the tissue portion for secondary inspection (which is a microscopy inspection) might not be indicative of all the pathological tissues contained in the tissue portion.

The present invention provides a novel tissue inspection system and a probe device for use in such system, where the probe configuration and controllable operation enables almost fully automatic and effective (high-quality) inspection of a tissue portion.

According to one broad aspect of the invention, there is provided a method for use in automated tissue sampling for pathology processing. The method comprises: applying tissue characterization inspection to a tissue portion and determining a spatial profile for at least one tissue property distribution within the tissue portion; analyzing data indicative of said tissue property spatial profile; and carrying out at least one of the following: generating and displaying an image indicative of said spatial profile thereby enabling a user to select one or more regions of said tissue portion to be collected for further analysis, and designing a pattern indicative of an arrangement of regions of the tissue portion, and generating an storing data indicative of said pattern, thereby enabling selection of at least one region of said tissue portion to be collected for further analysis.

It should be noted that the term tissue portion used herein may be an initial excised tissue specimen in the form of a volumetric structure (e.g. lump) and the inspection of such structure by the tissue characterization unit provides for identifying a sample or slice thereof to which further analysis (e.g. by microscopy) is to be applied. Alternatively, the tissue portion may be the tissue slice itself (e.g. previously identified in the tissue specimen, e.g. by the same tissue characterization unit, or provided by another suitable technique, such as manual slicing without prior tissue characterization), and the inspection of such slice by the tissue characterization unit provides for identifying a sample therein to be removed/collected for further analysis. Thus, the term region or tissue region as used herein signifies either a sample or a slice of the tissue portion.

According to another broad aspect of the invention, there is provided a probe device for use in a tissue inspection system. The probe device comprises: a probe body, and a control unit at least partially incorporated in the probe body. The probe body carries one or more functional units including at least a tissue characterization unit which is configured and operable to provide sensing data indicative of at least one tissue property at measurement locations in the tissue portion being held by the probe. The control unit comprises a processor utility configured and operable for receiving and processing the sensing data and generating measured data indicative of a spatial profile of said at least one tissue property distribution within the tissue portion. The control unit further comprises at least one of the following: an imaging utility for receiving and analyzing the measured data and generating and displaying an image indicative thereof thereby enabling a user to select of at least one region of said tissue portion to be collected for further analysis, and a pattern generator module configured for analyzing said measured data and determining a pattern indicative of an arrangement of regions in said tissue portion, thereby enabling selection of at least one of said regions for further analysis.

According to yet another broad aspect of the invention, there is provided a system for tissue inspection. The system comprises a probe device configured for holding a tissue portion and comprising at least a tissue characterization unit configured and operable to provide sensing data indicative of at least one tissue property at measurement locations in the tissue portion; and a control unit comprising a processor utility configured and operable for receiving and processing the sensing data and generating measured data indicative of a profile of said at least one tissue property at the different locations within the tissue along one or two axes, and at least one of the following: an imaging utility for receiving and analyzing the measured data and generating and displaying an image indicative thereof thereby enabling a user to select of at least one region of said tissue portion to be collected for further analysis, and a pattern generator module configured for analyzing said measured data and determining a pattern indicative of an arrangement of regions in said tissue portion, thereby enabling selection of at least one of the regions for further analysis.

The probe device may comprise at least one functional unit configured for holding the tissue portion and carrying said tissue characterization unit. The tissue characterization unit may be located inside the probe body, or on a surface of the probe body, or may be carried by a functional member projecting from the probe body. The probe device may include a plurality of functional members. In some embodiments, each or at least one of such functional members comprises an arm having a proximal end by which it is mounted on the probe body and a distal end carrying a functional unit, thereby enabling to apply at least two different functions to a tissue portion while on the probe device. If several functional units are used, then for example, at least one of the functional units may be configured for movement with respect to the at least one other functional unit. In this case, the control unit would comprise a movement controller configured and operable for controlling the movement of the functional unit(s). The tissue portion holder and the tissue characterization unit may be carried by the same functional member, or by different functional members.

At least some of utilities of the control unit may be incorporated in a probe body of the probe device; or the control unit is entirely incorporated inside the probe body or in a separate device connectable to the at least one functional unit (i.e. the tissue characterization unit).

The system may be configured to scan the tissue portion on the tissue holder by at least one sensor of the tissue characterization unit.

The system may further comprise a tissue collection unit configured and operable for collecting a tissue from the at least one selected region in the tissue portion, as well as may also include a cutting unit configured and operable for cutting from the tissue portion said at least one selected region. Such cutting may be actuated and operated automatically (or at least semi-automatically) by the control unit utilizing data indicative of the at least one selected region The control unit may be configured and operable for analyzing data indicative of position data, e.g. being the movement data about the movement of at least one of the functional units with respect to the other (typically, at least one of the tissue holder and tissue characterization units) and analyzing the sensing data, and determining the measured data indicative of the tissue property profile.

The tissue characterization unit may comprise an array of tissue characterization sensors capable of determining the at least one tissue property at the multiple measurement locations in the tissue portion. The control unit may be configured and operable for analyzing the sensing data and generating the tissue property profile for the multiple measurement locations in the tissue portion corresponding to locations of the tissue characterization sensors.

The tissue portion conditions that may be determined include but are not limited to a kind of pathology and/or a kind of tissue type.

The tissue property that can be sensed by the tissue characterization unit includes at least one of the following properties: optical, electro-magnetic, electrical conductivity, tactility, elasticity.

BRIEF DESCRIPTION OF THE DRAWINGS

In order to understand the disclosure and to see how it may be carried out in practice, embodiments will now be described, by way of non-limiting example only, with reference to the accompanying drawings, in which same reference numerals are used to identify elements or acts with the same or similar functionality, and in which.

It is noted that the embodiments exemplified in the figures are not intended to be in scale and are in diagram form to facilitate understanding and description.

DETAILED DESCRIPTION OF EMBODIMENTS

The present disclosure relates to a system and method for tissue inspection for, inter alia, diagnosing pathologies and/or classifying tissue types within a tissue specimen.

The system includes a probe which is associated with a control unit (referred to herein at times "control and processing unit"). The probe includes a body and one or more functional units which is/are mounted on said body or located thereinside. In some embodiments, the functional unit(s) is/are carried by the functional member(s) mounted on the probe body. Alternatively or additionally, the probe body may include a slot for locating the tissue portion therein, and one or more functional units embedded inside the probe body in a manner providing access to the tissue portion. In case more than one functional unit is used, at least one of the functional units can be mounted for movement with respect to the other thus implementing relative displacement between at least two functional units.

Generally, the probe includes at least one functional unit for holding a tissue portion and carrying one or more tissue characterization sensors configured and operable to provide sensing data indicative of a spatial profile of at least one tissue property distribution (e.g. values at multiple measurement locations) on the surface or within the tissue portion or in a part/slice thereof (e.g. by scanning).

The control unit may or may not be at least partially incorporated in the probe body. The control unit receives and processes the sensing data and generates measured data indicative of a profile/map of the at least one tissue property at the different locations within the tissue (along one or more axes). This measured data can be further processed and analyzed to enable selection of at least one region (sample or slice) thereof for further analysis, as will be described further below.

In some embodiments, the system further includes a tissue collection unit configured to capture (e.g. by cutting) a sample or slice of interest (constituting the tissue region) from the tissue specimen for further processing and analysis. Preferably, the system also includes a slicer unit used to divide the specimen into tissue slices.

In some embodiments, different functional units are carried by different functional members mounted on the same probe body. The functional members may be in the form of robotic arms projectable from the probe body, and configured to be maneuverable and extendable/retractable, and freely movable in three dimensions, relative to each other and relative to the probe's body.

Figure 1:
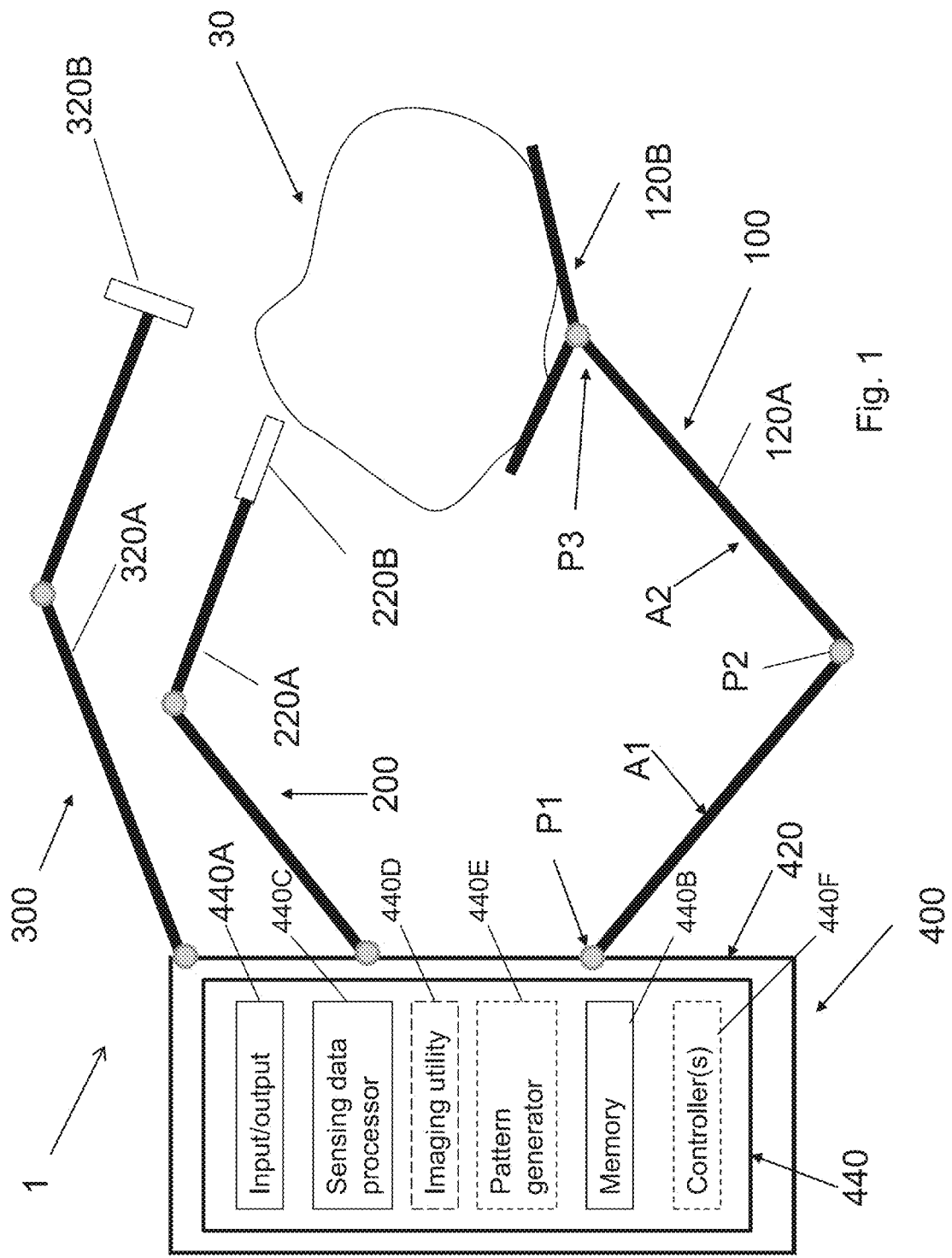
FIG. 1 is a schematic illustration of the functional units of a system according to an embodiment of the invention, for tissue inspection.

Referring to FIG. 1, there is illustrated an example of a tissue inspection system, generally designated 1, configured and operable in accordance with the present invention. The system 1 includes a probe 400 associated with a control unit 440. The probe has a probe body 420, and one or more functional members associated with one or more functional units—three such functional members 100, 200 and 300 being shown in the present specific non-limiting example, which are carried by the probe's body 420. In some embodiments, at least one functional member is movable with respect to at least one other functional member in such a way that allows relative displacement between respective functional units in three dimensions, as will be described more specifically further below.

In the present specific but not limiting example, the control unit 440 is shown as being incorporated within the probe body 420. However, it should be understood that the control unit 440 can be a stand-alone device positioned outside the probe body and connected to the functional unit(s) via wires or wireless signal transmission (e.g. RF, Bluetooth, acoustic, IR, etc.). In another embodiment, the utilities of the control unit are distributed in the probe body and the external control device. Preferably, the control unit is at least partially incorporated in the probe body.

The control unit 440 typically includes one or more controllers for the probe operation and one or more processing utilities for analyzing the tissue characterization data, as will be described more specifically further below. It should be noted that such controllers and processing utilities may be embedded in separate units, and therefore the term control unit should be interpreted broadly, as a single unit or multiple units that may be incorporated within the same or different enclosures. In every possible configuration, the communication between the functional units and the control and processing utilities (one or more units) is carried out with any suitable wiring or wireless technologies.

As indicated above, a relative displacement between at least two of the functional members is provided, as well as displacement of at least one functional unit (member) with respect to the probe's body. In the present example, the functional members 100, 200 and 300 include (robotic) arms 120A, 220A and 320A respectively, each having a proximal end by which it is connected to the probe body 420 and a distal end which serves for mounting thereon a functional unit. As shown in the figure, arms 320A, 220A and 120A carry functional units 320B, 220B and 120B respectively on their distal ends. Each of the arms 320A, 220A and 120A is mounted on the probe body in a manner allowing an angular displacement (i.e. pivotal movement) of the arm with respect to the probe body; to this end, a pivot P1 is appropriately provided. The arm of each functional member is composed of several sub-members (segments) pivotally/rotatably connected to one another by a hinge or pivot P2. Thus, the entire arm is retractable/extendable with respect to the probe body, and the movable segments of arm allow for more degrees of freedom in spatial allocation of the arm. In the non-limiting example of FIG. 1, each functional member (its robotic arm) consists of two such sub-members A1 and A2 connectable via pivot P2. It should, however, be understood that the invention is not limited to this specific example, i.e. limited to neither the provision of arms (movable or not) carrying the functional units outside the probe body nor to any specific number of functional units. Generally, the probe body is configured for holding a tissue portion and carriers at least a tissue characterization unit, as will be described further below.

In the present example, the functional member 100 is configured for holding a tissue portion under inspection. More specifically, the arm 120A of the functional member 100 at its proximal end is connected to the probe body 420, and at its distal end carries a specimen holder 120B (constituting a functional unit). The arm 120A of the functional member 100 has two sub-members A1 and A2 connected through a pivot P2. Each of the other two functional members 200 and 300 is configured similar to the member 100, namely its arm similarly has proximal and distal ends, and two sub-members pivotally connected to one another. The functional members 200 and 300 are configured for carrying out different functions and thus different functional units 220B and 320B can be mounted on the distal ends of their arms 220A and 320A. It should be understood that the probe may be configured for mounting various functional units on the arms of their functional members, as well as the arms may be of any suitable configuration allowing appropriate movement thereof in space and one with respect to the other.

The control unit 440 is typically a computer system including inter alia such hardware/software utilities as data input and output utilities 440A, memory 440B, CPU, etc. For the purposes of the present invention, the control unit 440, i.e. its CPU, includes a sensing data processor utility 440C, and either one or both of imaging utility 440D and pattern generator 440E which is/are connected to the processor utility 440C and operate(s) to enable a selection of one or more regions of the tissue portion from the tissue portion under inspection. More specifically, the processor utility 440C is configured and operable for receiving and processing sensing data (from the tissue characterization unit) and generating measured data indicative of a spatial profile of at least one tissue property distribution within the tissue portion. The imaging utility 440D receives and analyzes the measured data (e.g. previously stored in the memory 440B), and generates and displays an image indicative thereof, thereby enabling a user to select at least one region (e.g. sample or slice) of the tissue portion to be collected for further analysis. The pattern generator module 440E analyzes the measured data and determines a pattern indicative of an arrangement of regions (e.g. samples or slices) in said tissue portion (and preferably stores the pattern data in the memory), thereby enabling selection of at least one of these regions for further analysis. The pattern indicative of an arrangement of regions may also be displayed as an image, by use of the imaging utility 440D. The probe device may be provided with or connected to a display.

Optionally, the control unit 440 may also be equipped with movement controller(s), generally at 440F, connectable to drive units (not shown) of the pivots or the like movement mechanisms operating the movement of the functional unit(s)/associated arms (e.g. extension/retraction of the arms), thereby controlling relative positions of the different functional units. Thus, control of the arms' movement by the control unit 440 is executed via integral computer program/software, and it can be fully or partially automated, subject to the user preferences.

The control unit 440 preferably continuously monitors (registers and records in the memory) readings from the tissue characterization unit (i.e. sensing data) as well as the spatial coordinates of the sensing data (e.g. via the sensors' positions, and possibly also via the scan data, i.e. movement of sensor(s) and/or tissue portion with respect to one another). Also, the control unit may be used for controlling the operation (movement) of a cutting (sampling or slicing tool) and/or collection tool, so that the position in space of each such functional unit at each time during the probe operation can be definitely and accurately identified.

Thus, in the present example, the probe 400 carriers such functional units as specimen holder 120B, tissue characterization unit 220B, and tissue collection unit 320. The specimen holder 120B is configured and operable to receive and hold a tissue specimen 30 thereon, such that the specimen 30 is accessible and can be brought into interaction, either via physical contact or without it, with the other functional units 220B and 320B carried by the functional members 220A and 320A. The specimen holder 120B and the tissue specimen 30 thereon can be independently differently oriented in space due to flexible abilities of the multiple hinges/pivots of the respective arm 120A, and also can be differently oriented with respect to the other functional units, due to such flexible abilities of arm 120A and/or all the other arms of the functional members. These displacements are controlled by the control unit 440 to allow a full three dimensional access to the specimen 30 by the functional units 220B and 300B.

The tissue characterization unit 220B is configured for determining/measuring the tissue properties/conditions at different locations of the specimen 30 and providing sensing data indicative thereof. To this end, the tissue characterization unit 220B may include at least one tissue characterization sensor and be configured for scanning the specimen 30 by said at least one sensor. In some embodiments, the tissue characterization unit 220 includes a plurality of sensors, e.g. a one or two dimensional array (matrix) of sensors, which may measure the tissue properties in a respective array of locations inside or on the surface of the tissue while scanning the specimen or not. The sensing data is processed by the processor utility 440C which generates measured data corresponding to the tissue properties/conditions distribution within the surface of or inside the specimen.

The tissue characterization sensor(s) may be of any suitable type for determining various properties of the tissue indicative of the tissue condition, e.g. whether the tissue can be classified as normal or abnormal. Such properties may include one or more of the following: optical property (e.g. absorption/transmission, reflection, scattering, fluorescence), electro-magnetic property (reflection and/or transmission and/or absorption with respect to radio frequency, microwave, low frequency, medium frequency), dielectric property (e.g. electrical conductivity, permittivity), heat conductivity, humidity, tactility, and/or elasticity (e.g. shear modulus, elastic modulus, wave speed, scattering).

It should be noted that in order to generate a map of the tissue property distribution, the control unit may utilize the sensing data, and the position data (e.g. sensors' positions and/or scan data). Alternatively or additionally, the position data may be provided by using an imaging facility, e.g. acoustic or radiative (e.g. optical), for acquiring image or images of the tissue portion under inspection, and consequently combining the sensed data with the image data, e.g. overlaying the data indicative of the sensed signals on top of the image data thereby obtaining the map of the sensed data. It should thus be understood that in order to obtain the map/profile of the tissue characterization signals, at least one of the following may be used: scanning the tissue portion by one or more sensors, using static array/matrix of the sensors and/or combining the sensed data with the image data.

The sensor(s) may be of a so-called "passive" type or "active" type. In the latter case the tissue characterization unit generates incident signals (e.g. electrical or optical) and receives the tissue response to these signals.

For measuring optical, electro-magnetic and/or acoustic properties of the tissue portion e.g. by using active type sensors, the tissue characterization unit 220 may be configured to operate in a so-called reflection mode and/or scattering mode and/or transmission mode. If transmission and/or scattering mode is considered, the tissue characterization unit 220 may include two spaced-apart plates, e.g. defining a gap between them for a specimen to be located therein, each sensing plate containing a sensor or an array of sensors. One of the plates functions as a transmitter and the other as a receiver, or it is possible that each one of the plates functions as a transceiver.

It should be understood that in the embodiment where the probe is configured for holding a tissue specimen and measuring the tissue properties, and the tissue characterization sensors are arranged in a matrix, such functional units as specimen holder and tissue characterization unit may be combined in a single functional member. For example, a specimen holding plate (being a part of unit 120B or 220B) may carry a matrix of tissue characterization sensors, such that when the specimen is put on said holding plate the sensors are beneath the specimen 30 enabling measurements of the tissue properties at different locations inside the tissue, or on the surface of the tissue, aligned with the sensors. Practically, this configuration is more suitable for measuring/inspecting a thin tissue slice, but generally may be used in measuring in volumetric specimens. Also, the tissue holding element may have a cap-like or polygonal-like configuration and its curved surface may carry a three-dimensional array of sensors.

The scanning/sensing carried out by the tissue characterization unit 220 may be carried out according to a predetermined preprogrammed sequence, controlled by the software module of an appropriate scan controller that may be integrated within the control unit 440, to thereby measure at multiple locations in the outer surfaces of the tissue specimen 30. For example, the tissue characterization unit 220 may scan the specimen 30 from point to point, by moving the tissue characterization unit 220 along the specimen's surface, while maintaining a working distance between the sensor(s) and the specimen's surface; to this end, the tissue characterization unit (its sensing surface) may be controllably lowered/lifted to be sufficiently close to the specimen's surface and controllably moved to successive measurement locations in the specimen. The arms 120A and 220A (the drive mechanism of their pivots) of the functional members 100 and 200 are operated by the control unit to rotate and move mutually to cover all needed orientations.

Output data from the sensor(s) is processed by the processing module 440C of the control unit 440 and the tissue property/condition is determined for each measurement/sensed location (constituting sensing data). By concurrently monitoring/recording the measurement locations in/on the tissue specimen (e.g. spatial coordinates of the specimen holder 120B and the tissue characterization unit 220B, and/or the coordinates of the sensors in the matrix), the spatial profile of the tissue property distribution within the specimen can be determined.

As described above, the probe may include the tissue collection unit 320B carried by the arm 320A of the functional member 300. The tissue collection unit 320B may be configured to cut a sample/slice of interest (e.g. which has been classified by the preliminary inspection of the specimen 30 as containing a potentially abnormal tissue) for additional inspection and analysis. The tissue collection unit 320B may be activated/operated by the control unit or manually by operator via user interface of the control unit, to collect the tissue sample/slice of interest at the defined location(s) based on the sensing data from the tissue characterization sensors. The scanning of the exterior of whole specimen 30 may not be sufficient, as the pathologies or different kinds of tissue types are located deeply inside the specimen 30 and not superficially. In these cases, there is a need to further sense and characterize deep regions of the tissue specimen. Accordingly, the intact specimen is sliced into sections, see FIG. 2, and the slices are further inspected. To do this, the tissue characterization and analysis system of the present invention may comprise a specimen slicer unit being mounted at a distal end of another arm of a functional member which is not specifically shown here. Slicing can also be performed manually.

As indicated above, the probe may generally include at least one functional member. For example, this may be one functional member configured for holding the tissue portion and also carrying the tissue characterization sensors; or two functional members carrying respectively the tissue holder and tissue characterization unit. Additionally, the functional member(s) carrying a slicer and/or collection unit(s) may be used.

Figure 2:
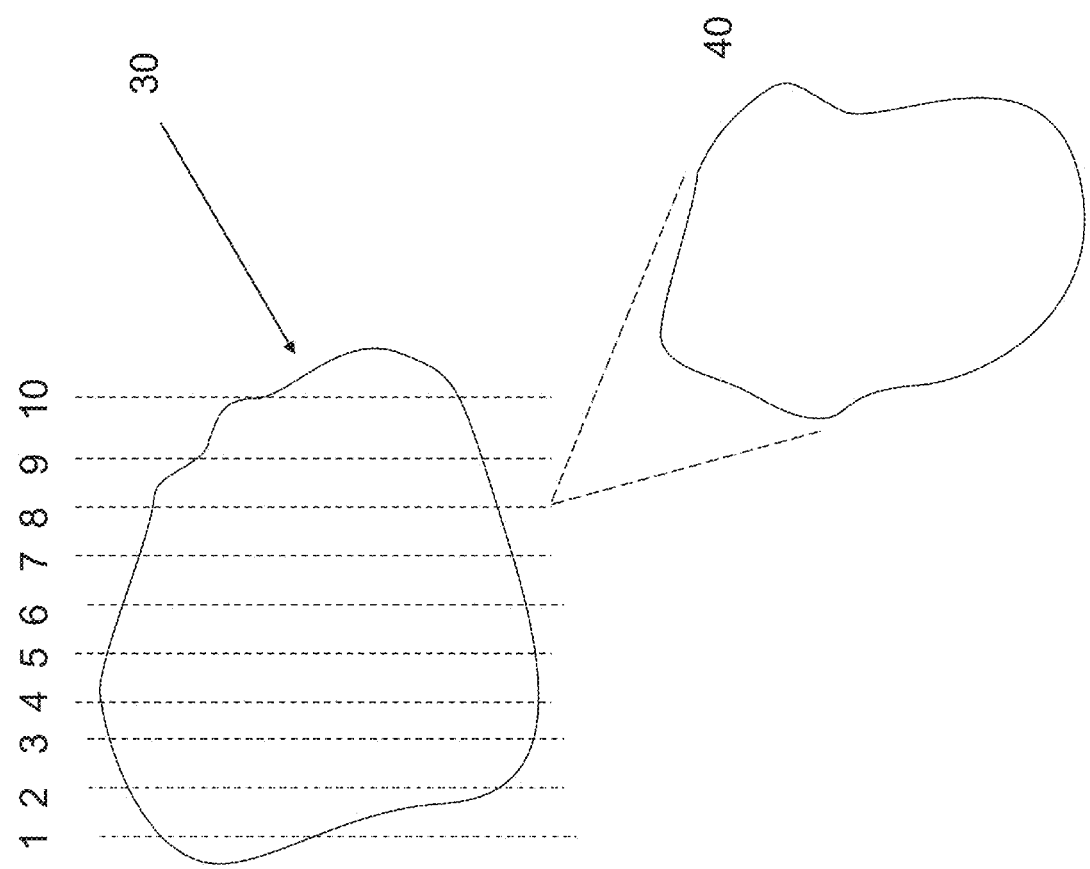
FIG. 2 illustrates the principles of sample slicing technique where the tissue specimen is divided into a number of regions (slices) to be scanned/examined separately using the system of the invention.

The tissue specimen 30 may be cut into several thin slices to enable access to every point in the specimen 30. This is schematically illustrated in FIG. 2 showing the tissue specimen 30 being sliced into 11 thin slices, and an exemplary slice designated 40 being collected for further inspection. It should be understood that the slices may be of equal or different thicknesses. The positions and spacing of the slicing lines may be determined manually, by the operator/technician. The operator/technician may also use information based on the imaging data generated and displayed by the imaging utility 440D to determine the positions and spacing of the slicing lines. Alternatively or additionally, the positions and spacing of the slicing lines (defining the slice thickness) may be determined by the pattern generator 440E (software module) of the control unit 440. The pattern generator receives initial measured data of the whole specimen 30 (e.g. from tissue characterization unit 220B carried by the probe or another tissue characterization device), where this measured data is indicative of the profile of tissue property(ies) distribution within the specimen (along at least one axis), which can be determined using the recorded spatial locations of the functional units and/or sensors, as described above. Thus, generally speaking, the system of the invention allows automatic, semi-automatic or manual identification of a sample or slice to be selected (e.g. removed) for further analysis.

It should be noted, and indicated above, that the term "tissue portion" or "tissue specimen" under inspection, being held by the probe actually refers to either an initial excised tissue before being divided to samples or slices or the tissue sample/slice separated after identifying respective locations during the previous inspection of the initial tissue portion. It is thus possible that the slicing procedure has already been made beforehand, e.g. manually or by a separate suitable slicer, and the characterization/analysis carried out by the system of the invention is done directly on the tissue slices. In this case, the analysis of the whole tissue specimen as well as slicing/collection procedures, if any, may be carried by the system of the invention or by separate appropriate utilities.

Figure 3:
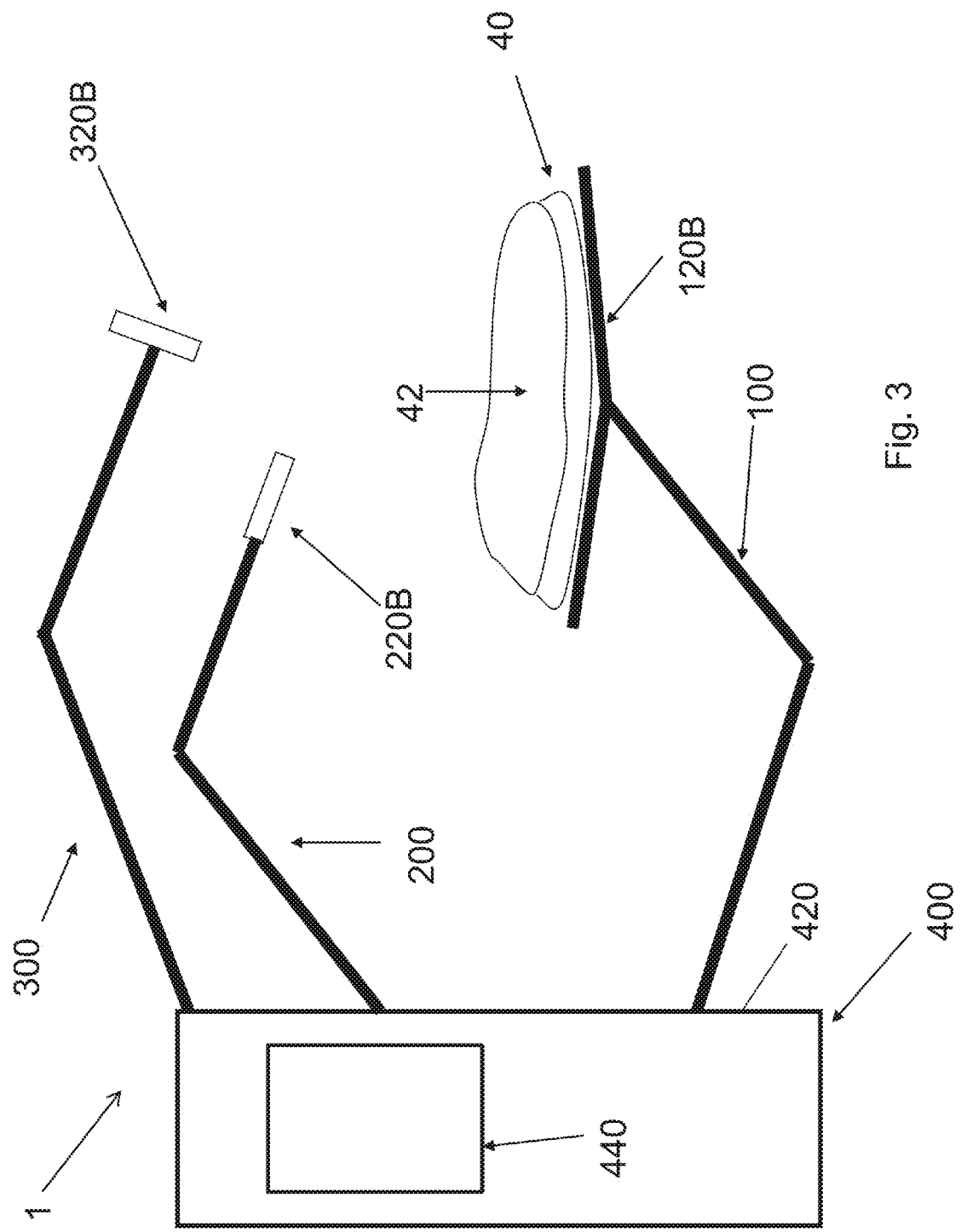
FIG. 3 is a schematic illustration of how the system of FIG. 1 can be used for sensing/examining a tissue slice.

Reference is made to FIG. 3 illustrating the above-described system 1 of the invention operating for inspecting a separate tissue slice 40. Thus, in the example of FIG. 3, the specimen holder 120B holds the slice 40 instead of the volumetric specimen 30 as in FIG. 1. As indicated above, there might not be a need to move the specimen holder 120B and/or the tissue characterization unit 220B, as well as the tissue collection unit 320B, in three dimensions, relative to each other, and the movement may be restricted to two dimensions (i.e. movement within a plane substantially parallel to the slice surface), as the thin slice 40 needs to be inspected only from its side/surface 42 facing the tissue characterization unit 220B. At times, it might be required to scan/sense both of the tissue slice's surfaces, then the slice may be flipped on its other side and further scanning/sensing is carried out or the tissue characterization unit includes two sensing members (each including one or more sensors) arranged with a gap between them for locating the tissue slice in said gap.

Figure 4:
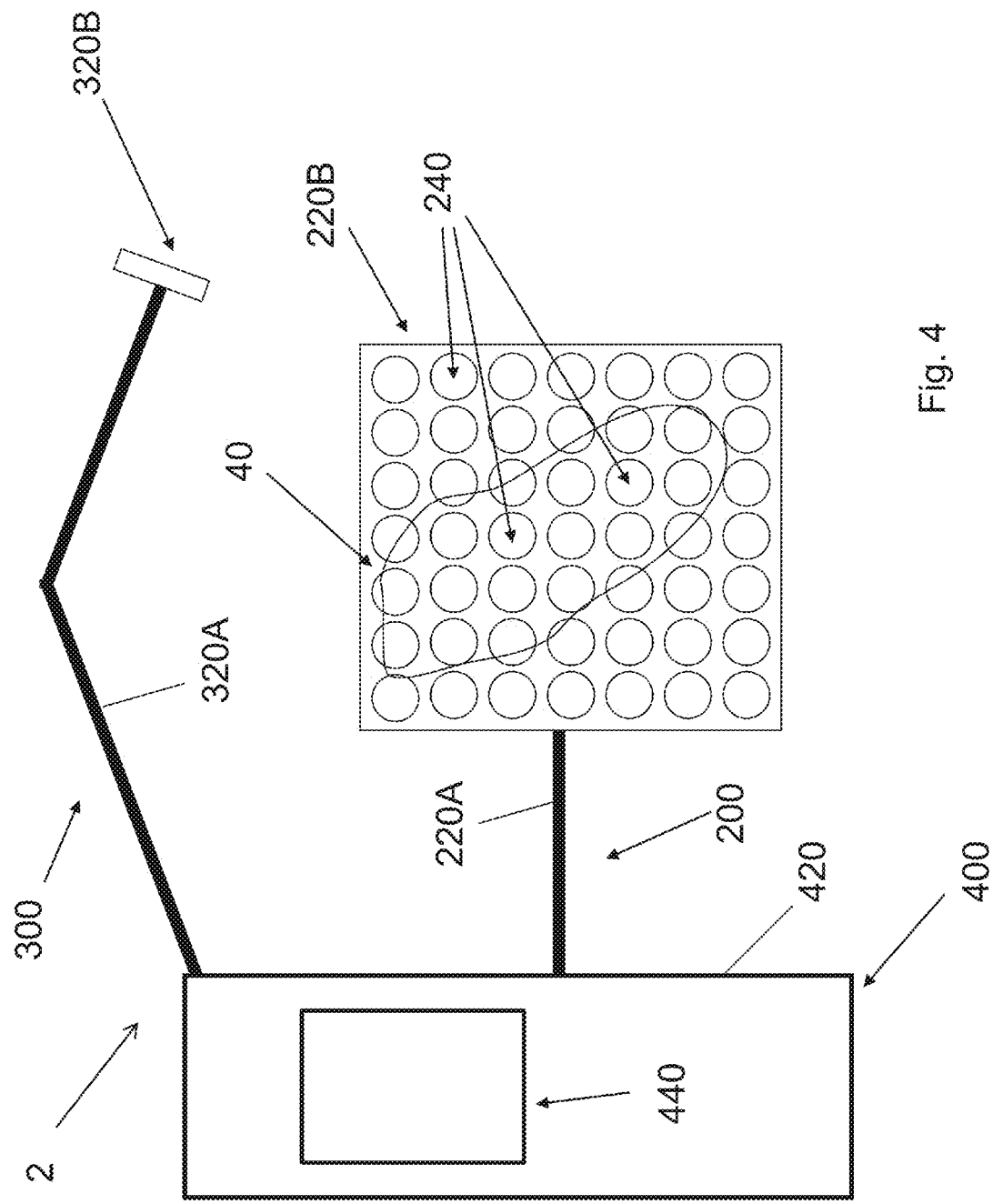
FIG. 4 is a schematic illustration of a system of the invention utilizing a matrix of tissue characterization sensors for examining the tissue slices, FIG. 5 exemplifies the principles of inspecting a tissue slice using the technique of the invention.

Reference is made to FIG. 4 exemplifying another embodiment of the system, generally designated 2, according to the invention. To facilitate understanding, the same reference numbers are used for identifying components that are common for all the examples. In this example, the probe includes two functional members 200 and 300 mounted on the probe body 420. The control unit 440 is configured generally as described above with reference to FIG. 1, and may be entirely incorporated in the probe body, or in a stand-alone computer system, or its utilities may be distributed between the probe body and the external system.

The functional members carry a tissue characterization unit 220B and a tissue collection unit 320B, and the specimen holding function is carried out by the tissue characterization unit 220B. In other words, the tissue holding and characterization functions are combined by the same functional member. In this example, the tissue slice 40 (supplied or previously prepared/cut, e.g. in view of the inspection results of the entire sample 30) is positioned directly on top of the sensing surface of the tissue characterization unit 220B. The sensing surface is defined by a plurality of sensors 240, forming in this specific example a 7×7 two dimensional matrix of sensors.

It should be noted, and specifically indicated above, that the functional unit or units may be accommodated inside the probe body and not necessarily carried by a functional member/arm projecting from the probe body. Also, the arm (if used) may or may not be movable.

Each sensor in the array senses the nearby portion of slice 40 (within the sensing region or "field of view" of the sensor) and sends measured data to the control unit 440 for analysis. The number of sensors 240 in the array or matrix may depend on the specific application, as well as the area of the slice to be inspected and other relevant factors. The sensors 240 may be of the same kind utilizing the same modality and measuring the same or similar properties, or may involve different characterization modalities enabling measuring different tissue properties at the same location/s in the tissue portion.

In this connection, no scanning would occur or be needed. The tissue characterization unit 220B does not scan the slice 40 and no relative movement or displacement occurs between the slice 40 and the tissue characterization unit 220B. The different regions/locations of the slice 40 are sensed by the different sensors 240 in the vicinity of said regions and the measured data is indicative of the measured tissue property(ies) and the respective location. This would simplify the processing stage as no fitting between spatial locations of the functional arms is required during the phase of tissue characterization. Furthermore, it is possible to characterize the tissue properties accurately due to the large number of sensors with known static locations, and due to the wide possibilities of applying different algorithms and protocols regarding data collection and analysis.

The system of the present invention provides for effective tissue sampling and analysis (e.g. histological examinations carried out in order to identify tissue types such as tumors) while utilizing a simple and accurately controllable probe configuration and operation.

Figure 5:
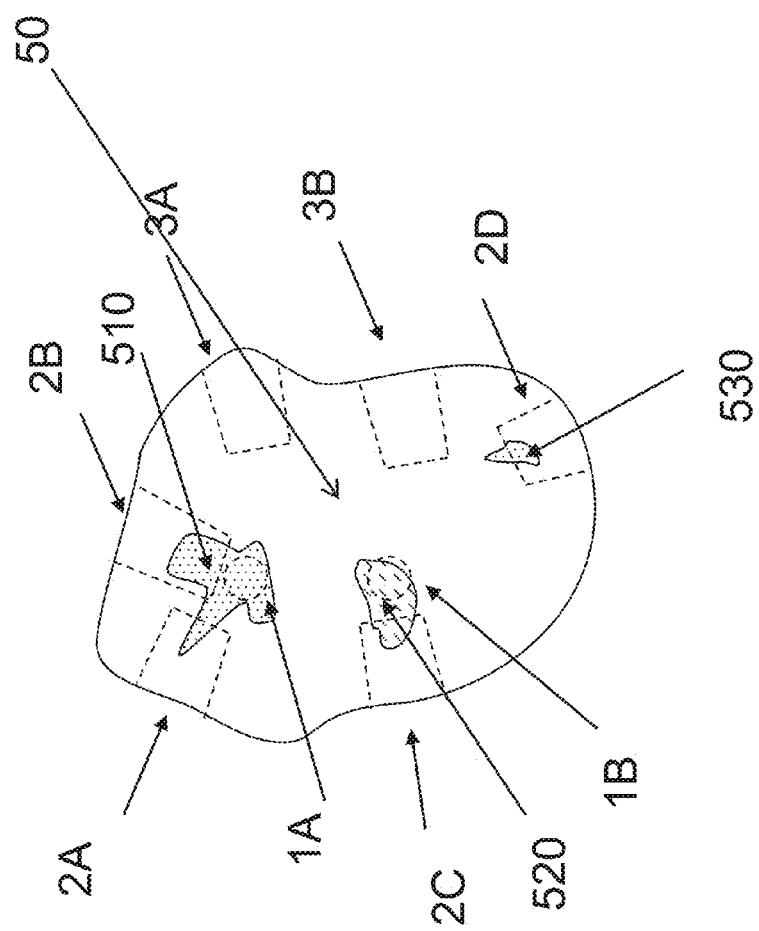

It should be understood that according to the conventional techniques of the kind specified, a tissue specimen is initially examined by bare eyes, and then sections of concern (identified as potentially abnormal) are cut out by the professional for additional microscopy-based analysis. FIG. 5 illustrates a tissue slice 50 having different tissue types/pathologies marked 510, 520 and 530. The professional performs visual inspection and can generally identify the existence of some abnormality in the tissue slice. Then, the professional cuts several tissues sections along the circumference of the slice margin, and the cut sections might include sections 2A-2D which include parts of the abnormal tissues aimed at evaluating the extent of the abnormality, and might also include sections 3A and 3B free of abnormal tissues and sections 1A and 1B from the grossly appearing abnormalities, for the purposes of characterizing the tissue types. Such sectioning is strongly dependent on the visual inspection capabilities of the professional, hence involving subjectivity and risk of wasted work.

Utilizing the system of the present invention, it is possible to overcome these deficiencies. By the fully automated characterization applied with the system, it becomes possible to directly identify the abnormal/suspicious tissue regions 510, 520 and 530 and optimize the cutting and collection of parts/sections mentioned above (1A-B, 2A-D and 3A-B) by using a sampling pattern module of the control unit 440, as described above. It should be noted that the abnormal/suspicious tissue regions that can be identified by utilizing the system of the present invention are not the same as those that would have been identified by the use of naked eye. In general, not all abnormal/pathological tissue regions can be identified by visual inspection. It should be also noted, that the present invention may be utilized to only provide the sampling/slicing plan, including the relevant measured tissue property/ies and the tissue slice image, and the cutting/collection of the samples/slices may be performed later manually by a professional or by separate automatic or semi-automatic tool(s).

Figure 6:
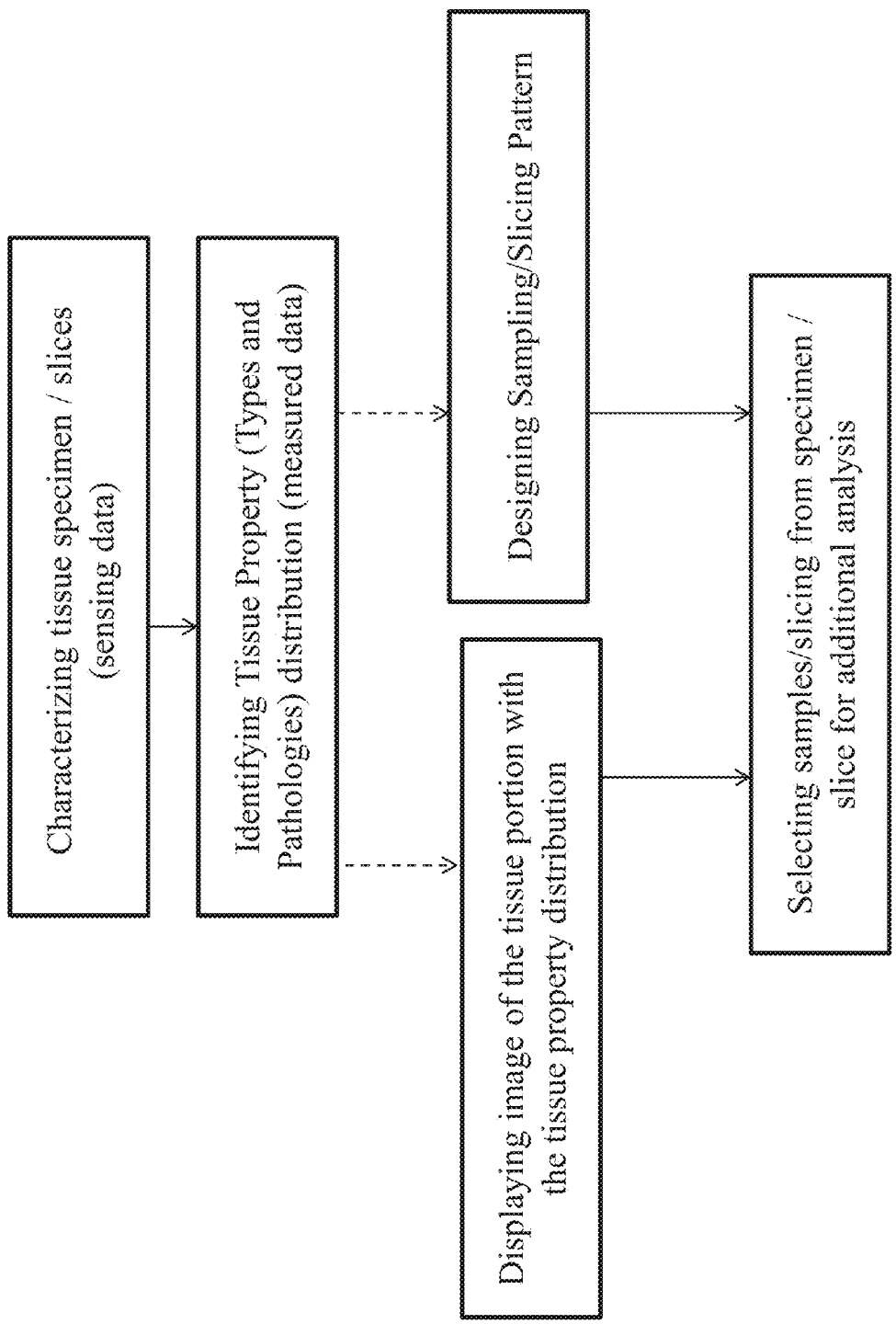
FIG. 6 is a diagram exemplifying a method of the invention for automated or semi-automated tissue inspection enabling selection of a tissue region for pathology processing.

Reference is made to FIG. 6 exemplifying a method of the invention for automated tissue selection (sampling) for pathology processing which can be carried out by the above-described systems. As shown in the figure, initially, the system may be operated to inspect the specimen or slice (e.g. by scanning), and, upon identifying and locating potentially abnormal tissues, is operated to either design an automatic sampling/slicing pattern (plan) accordingly. The system (the imaging utility of the control unit) may utilize measured tissue properties and respective locations in the tissue specimen based on the spatial coordinates of the functional units and possibly sensors in the matrix as recoded during the measurements, and deliver the image of the tissue portion with the tissue property distribution therein to the professional who decides when/where to take samples or activate an automated sampling. Additionally or alternatively, the system utilizes the measured data (sensed tissue properties and respective locations/position data, and generates a pattern of the slices/samples enabling to select (manually or semi- or fully-automatically), according to certain criteria, the sections/slices to be cut out of the specimen/slice, e.g. as exemplified in FIGS. 2 and 5.

The tissue samples can then be collected from different parts of interest in the specimen/slices for additional processing and slide analysis, using various methods such as staining and relevant protocols. The spatial locations of the collected tissue samples may be properly recorded to enable reconstruction of the specimen pathology status via appropriate software.

The above examples and description have of course been provided only for the sole purpose of illustration, and are not intended to limit the disclosure in any way. As will be appreciated by the skilled person, the invention can be carried out in a great variety of ways, employing more than one technique from those described above, all without exceeding the scope of the disclosure.

The invention claimed is:

1. A probe device for use in a inspection of an excised tissue portion, the probe device comprising:
a probe body carrying at least a tissue holder unit and a tissue characterization unit; the tissue holder unit having a surface for holding the excised tissue portion thereon such that the tissue is accessible by the tissue characterization unit; tissue characterization unit comprising one or more tissue characterization sensors arranged and configured for scanning at least a surface of the excised tissue portion when on said tissue holder unit, thereby providing sensing data indicative of at least one tissue property at measurement locations in the excised tissue portion being held by the tissue holder unit;
a control unit at least partially incorporated in said probe body, the control unit comprising:
a processor utility configured and operable for receiving and processing the sensing data and generating measured data indicative of a spatial profile of said at least one tissue property distribution within the surface or inside the excised tissue portion; and
at least one of the following:
an imaging utility for receiving said measured data and generating and displaying an image indicative thereof thereby enabling a user to select a region of the excised tissue portion for further analysis; and
a pattern generator module configured for receiving and analyzing said measured data and determining a pattern indicative of an arrangement of regions in the excised tissue portion, thereby enabling selection of at least one of the regions for further analysis.

2. The probe device of claim 1 comprising at least one functional member configured for holding both of said tissue holder unit and said tissue characterization unit.

3. The probe device of claim 1, wherein the tissue characterization unit is located inside the probe body, or on a surface of the probe body, or is carried by a functional member projecting from the probe body.

4. The probe device of claim 1, comprising a plurality of functional members, each functional member comprising an arm having a proximal end by which it is mounted on the probe body and a distal end carrying a functional unit, thereby enabling to apply at least two different functions to an excised tissue portion while being held by the probe device.

5. The probe device of claim 1, wherein at least one of the functional units is configured for movement with respect to the at least one other functional unit.

6. The probe device of claim 5, wherein the control unit is characterized by at least one of the following: (i) comprises a movement controller configured and operable for controlling the movement of said at least one functional unit; and (ii) is configured and operable for analyzing data indicative of the movement and the sensing data and determining said measured data indicative of the tissue property profile.

7. The probe device of claim 1, further comprising at least one of the following: a tissue sample collection unit configured and operable for collecting tissue from said at least one selected region in the excised tissue portion; and a cutting unit configured and operable to utilize data indicative of the at least one selected region for cutting said at least one region from the excised tissue portion.

8. The probe device of claim 1, wherein the tissue characterization unit comprises an array of tissue characterization sensors capable of determining said at least one tissue property at the multiple measurement locations in the excised tissue portion, the control unit being configured and operable for analyzing the sensing data and generating the tissue property profile for the multiple measurement locations in the excised tissue portion corresponding to locations of the tissue characterization sensors.

9. The probe device of claim 1, wherein the tissue characterization unit is configured and operable to determine at least one of the following tissue properties: optical, electro-magnetic, electrical conductivity, tactility, elasticity.

10. The probe device of claim 1, wherein the tissue characterization unit is configured and operable in either one or more of the following: a reflection mode, transmission mode, and scattering mode for determining said at least one property of the tissue.

11. A system for use in biological tissue inspection of an excised tissue portion, the system comprising:
a probe device comprising at least a tissue holder unit and tissue characterization unit; said tissue holder unit having a surface for holding the excised tissue portion thereon such that the tissue is accessible by the tissue characterization unit; said tissue characterization unit comprising one or more tissue characterization sensors arranged and configured for scanning at least a suface of the excised tissue portion when on said tissue holder unit, thereby providing sensing data indicative of at least one tissue property at measurement locations in the excised tissue portion;
a control unit comprising:
a processor utility configured and operable for receiving and processing the sensing data and generating measured data indicative of a spatial profile of said at least one tissue property distribution within the surface or inside the excised tissue portion, and at least one of the following:
an imaging utility for receiving said measured data and generating and displaying an image indicative thereof thereby enabling a user to select a region of the excised tissue portion for further analysis; and
a pattern generator module configured for receiving and analyzing said measured data and determining a pattern indicative of an arrangement of regions in the excised tissue portion, thereby enabling selection of at least one of the regions for further analysis.

12. The system of claim 11, wherein the control unit has one of the following configurations: (a) at least some of utilities of the control unit are incorporated in a probe body of the probe device; and (b) the control unit is incorporated inside a probe body of the probe device.

13. The system of claim 11, having one of the following configurations: (1) the probe device comprises at least one functional member configured for holding both the tissue holder unit and (2) the tissue characterization unit comprises a plurality of functional members, each functional member comprising an arm having a proximal end by which it is mounted on the probe body and a distal end carrying a functional unit, thereby enabling to apply at least two different functions to an excised tissue portion while on the probe device.

14. The system of claim 11, wherein the tissue characterization unit is located inside the probe body, or on a surface of the probe body, or is carried by a functional member projecting from the probe body.

15. The system of claim 11, wherein the probe device comprises a plurality of functional units comprising at least tissue holder unit and said tissue characterization unit, at least one of the functional units being configured for movement with respect to the at least one other functional unit.

16. The system of claim 11, further comprising at least one of the following: a tissue collection unit configured and operable for collecting a tissue from said at least one selected region in the excised tissue portion; and a cutting unit configured and operable to utilize data indicative of said at least one selected region for cutting from the excised tissue portion said at least region.

17. The system of claim 11, wherein the tissue characterization unit comprises an array of tissue characterization sensors capable of determining said at least one tissue property at the multiple measurement locations in the excised tissue portion, the control unit is configured and operable for analyzing the sensing data and generating the tissue property profile for the multiple measurement locations in the excised tissue portion corresponding to locations of the tissue characterization sensors.

18. The system of claim 11, wherein the tissue characterization unit is configured and operable to determine at least one of the following tissue properties: optical, electro-magnetic, electrical conductivity, tactility, elasticity.

19. A method for use in tissue inspection of an excised tissue portion, the method comprising:
applying tissue characterization inspection to at least a surface of the excised tissue portion and determining a spatial profile for at least one tissue property distribution on the surface or inside the excised tissue portion;
analyzing data indicative of said tissue property profile; and
carrying out the following:
generating and displaying an image of the excised tissue portion with the tissue property distribution therein, thereby enabling a user to select at least one region in the excised tissue portion for further analysis;
designing a pattern indicative of an arrangement of regions in the excised tissue portion, and generating and storing data indicative of said pattern, thereby enabling selection of at least one region in the excised tissue portion for further analysis.

20. The method of claim 19, further comprising at least one of the following: utilizing data indicative of said at least one selected region and operating a cutting unit for cutting said at least one region of the excised tissue portion for further analysis; applying secondary tissue characterization inspection to at least one selected region from said arrangement of regions; and utilizing stored data indicative of locations of one or more of the regions satisfying a predetermined condition of the tissue property and reconstructing the tissue condition of the excised tissue portion.

* * * * *

UNITED STATES PATENT AND TRADEMARK OFFICE
CERTIFICATE OF CORRECTION

PATENT NO. : 9,217,739 B2
APPLICATION NO. : 14/123249
DATED : December 22, 2015
INVENTOR(S) : Dan Hashimshony et al.

It is certified that error appears in the above-identified patent and that said Letters Patent is hereby corrected as shown below:

In the Claims

Claim 1, column 12, line 8, add the word --the-- before the word "tissue".

Claim 15, column 14, line 7, add the word --said-- before the words "tissue holder".

Signed and Sealed this
Seventh Day of June, 2016

Michelle K. Lee
*Director of the United States Patent and Trademark Office*